US008201186B2

(12) United States Patent  
Wei et al.

(10) Patent No.: US 8,201,186 B2  
(45) Date of Patent: Jun. 12, 2012

(54) INFORMATION ENCODING FOR ENABLING AN APPLICATION WITHIN A DIFFERENT SYSTEM/APPLICATION IN MEDICAL IMAGING

(75) Inventors: Guo-Qing Wei, Plainsboro, NJ (US); Qian Jianzhong, Princeton Junction, NJ (US); Feng Ma, Pennington, NJ (US); Xiaolan Zeng, Princeton, NJ (US); Cheng-Chung Liang, West Windsor, NJ (US); Li Fan, Belle Mead, NJ (US); Hong Chen, Plainsboro, NJ (US)

(73) Assignee: Edda Technology, Inc., Princeton Junction, NJ (US)

( * ) Notice: Subject to any disclaimer, the term of this patent is extended or adjusted under 35 U.S.C. 154(b) by 978 days.

(21) Appl. No.: 12/188,778

(22) Filed: Aug. 8, 2008

(65) Prior Publication Data

US 2009/0044199 A1 Feb. 12, 2009

Related U.S. Application Data

(60) Provisional application No. 60/954,738, filed on Aug. 8, 2007.

(51) Int. Cl.  
*G06F 3/00* (2006.01)
(52) U.S. Cl. .................................................. 719/313
(58) Field of Classification Search .................. None  
See application file for complete search history.

(56) References Cited

U.S. PATENT DOCUMENTS

| | | | | |
|---|---|---|---|---|
| 5,668,998 A * | 9/1997 | Mason et al. | ................. | 717/104 |
| 6,643,406 B1 | 11/2003 | Hajjahmad et al. | | |
| 7,054,473 B1 | 5/2006 | Roehrig et al. | | |
| 2002/0016718 A1 | 2/2002 | Rothschild et al. | | |
| 2003/0184811 A1* | 10/2003 | Overton | ....................... | 358/3.27 |
| 2004/0086163 A1 | 5/2004 | Moriyama et al. | | |
| 2005/0144482 A1* | 6/2005 | Anuszewski | .................. | 713/201 |
| 2006/0045306 A1* | 3/2006 | Cordery et al. | ............... | 382/100 |
| 2007/0040833 A1 | 2/2007 | Buyanovski | | |

OTHER PUBLICATIONS

Rada Hussein, Uwe Engelmann, Andre Schroeter, and Hans-Peter Meinzer, "DICOM Structured Reporting: Part 1. Overview and Characteristics", RadioGraphics, vol. 24, No. 3, May-Jun. 2004.*  
International Search Report and the Written Opinion of the International Searching Authority issued in International Application No. PCT/US08/72621 dated on Nov. 4, 2008.

* cited by examiner

*Primary Examiner* — Andy Ho  
*Assistant Examiner* — Paul M Kim  
(74) *Attorney, Agent, or Firm* — SNR Denton US LLP

(57) ABSTRACT

Methods and system for data/process sharing between different systems. A trigger response unit is deployed on a first system where a first application resides. The trigger response unit is to detect when a representation corresponding to trigger data from a second application is present in the first application. When such a presence is detected, the detected representation corresponding to the trigger data is decoded to obtain a trigger, wherein the representation encodes the trigger corresponding to the second application and information associated with data. Based on the trigger, the first system launches the second application within the first application on the first system by utilizing the trigger data that include a trigger pattern present in a trigger image.

29 Claims, 13 Drawing Sheets

INFORMATION ENCODING FOR ENABLING AN APPLICATION WITHIN A DIFFERENT SYSTEM/APPLICATION IN MEDICAL IMAGING

CROSS REFERENCE TO RELATED APPLICATION

This application claims priority under 35 U.S.C. §119 from Provisional Patent Application No. 60/954,738 filed on Aug. 8, 2007. The entire subject matter of the application is incorporated herein by reference.

BACKGROUND

1. Technical Field

The present teaching relates generally to method and system for process sharing between different system platforms. Specifically, the present teaching relates to method and system for information encoding for process sharing and communication between different medical imaging system platforms.

2. Discussion of Related Art

With the large number of applications available on computing devices, there is a need to allow these applications to share with each other data created in different applications. One conventional solution is through a set of interfaces such as Object Linking and Embedding (OLE) developed by Microsoft. Such interfaces can be used to facilitate creating a compound document, in which objects or data from different applications reside in a single document and such objects or data may be manipulated in an environment similar to its native environment in which these objects or data are initially generated. This is possible because an application may be embedded within an object or data it creates and imported as an integrated object into a document operated by a different application so that the former application may be invoked to manipulate its object within the document when needed. For example, within a Microsoft Word document, one may incorporate a Microsoft Excel sheet embedded with the Microsoft Excel application. When the Word document is opened, one may invoke Microsoft Excel editing tool within the Word (for embedding) to process the incorporated Microsoft Excel spreadsheet.

In medical imaging, there is a similar need. A patient data processed in one application system such as a dedicated clinical application system (or a server based thereupon) may be imported into a different data processing environment and further being viewed and/or interactively manipulated using tools of the first application within the environment of the system to which the patient data is exported. As a specific example, a Computer-Aided Detection (CAD) system may process patient data to identify locations of suspicious regions for, e.g., tumors, and such identified locations may be exported, with possibly other associated data such as patient information and the original imaging data, to another medical imaging analysis application such as a Picture Archiving and Communication System (PACS) environment, which is physicians' routine reading environment. Within the PACS environment, the physicians may need to invoke the CAD application on the same patient data and to use the CAD system's interactive tools to further analyze the data.

Existing systems in medical imaging utilize certain commonly conformed standard in medical imaging such as Digital Imaging and Communication in Medicine (DICOM). To share images of different modalities, DICOM specifies how images may be stored and transferred. However, DICOM does not allow data to be embedded with application(s) that creates the data, making it difficult, if not impossible, to manipulate data created in one medical imaging system to be manipulated in its native environment in a different application system.

With the current technical limitations in medical imaging, to share the result data generated by an application among different medical imaging systems and most importantly, to involve an application within different applications/systems, there are two existing solutions. One is simply sending the result data created in a first application to a second application in a recognizable format such as DICOM for display in the second application and for manipulation using tools of the second application. With this solution, manipulation using data tools of the first application system in the environment of the second application system is not possible. The second solution is to integrate the first application system such as CAD system with the second application system such as PACS through some mutually defined APIs. In this case, implementing the API-based integration requires code-level engineering effort, which can be not only time consuming but also cost prohibitive. For example, considering the complexity of CAD systems and PACS systems on today's market, the effort to achieve such API-based integration can be very costly. This kind of integration is especially difficult if one considers integration with systems already installed in a clinical environment. Other dedicated clinical applications, such as 3D visualization, have similar restrictions in their accessibility within another independent system. Therefore, there is a need for sharing data or process between different systems without having to incur a high cost or engineering difficulties.

BRIEF DESCRIPTION OF THE DRAWINGS

The inventions claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 7b shows the quadtree subbands of the wavelet transform of the encoding image as illustrated in FIG. 7a;

DETAILED DESCRIPTION

The present teaching is for providing process sharing and communication by encoding an application trigger and patient data ID into grayscales, locations, and frequencies of encoding objects and/or images without the need for developing APIs or code-level integration between two systems.

Figure 1A:
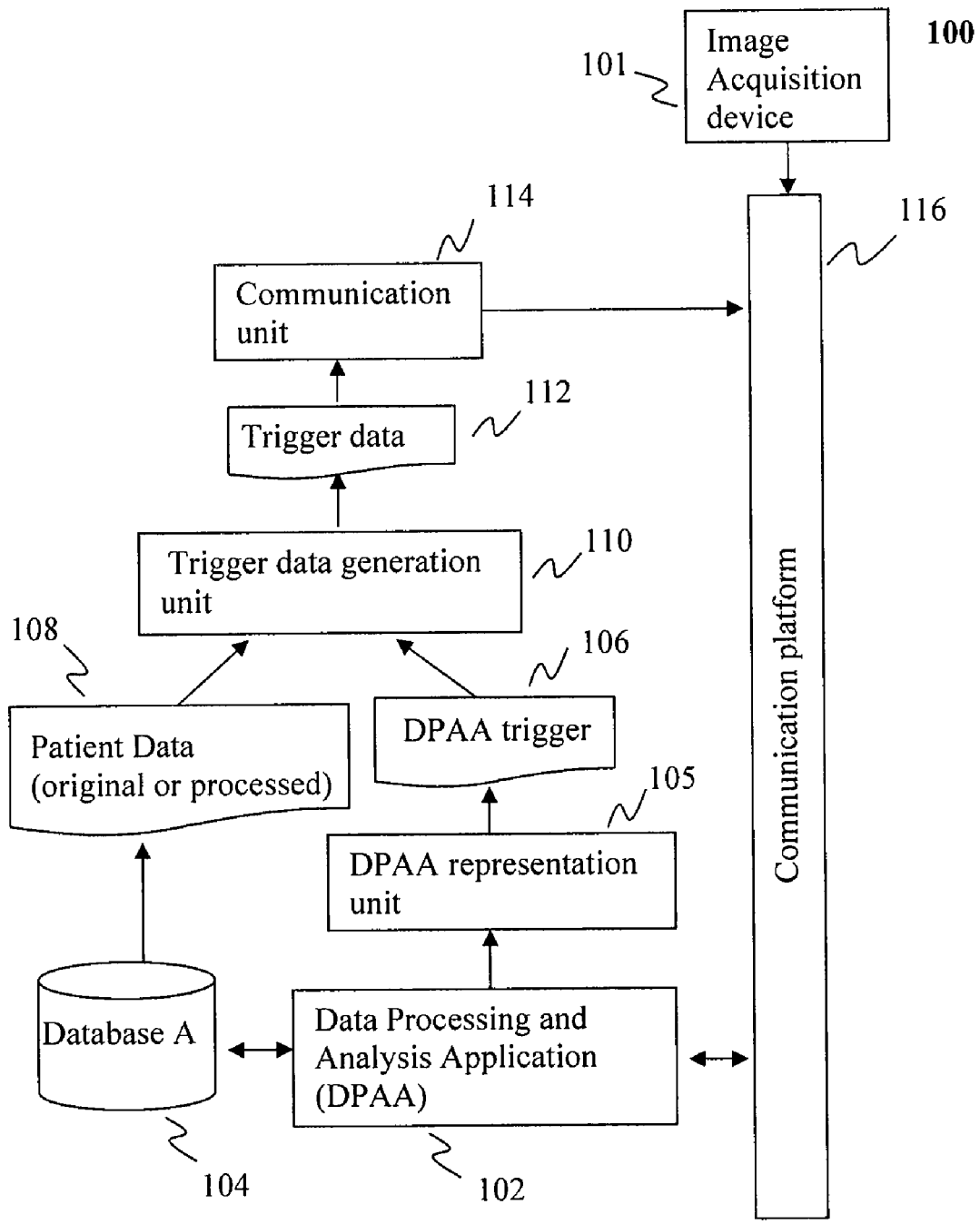
FIGS. 1a and 1b depict an exemplary construct of a system diagram for process sharing between two independent systems/applications, according to an embodiment of the present teaching.
Figure 1B:
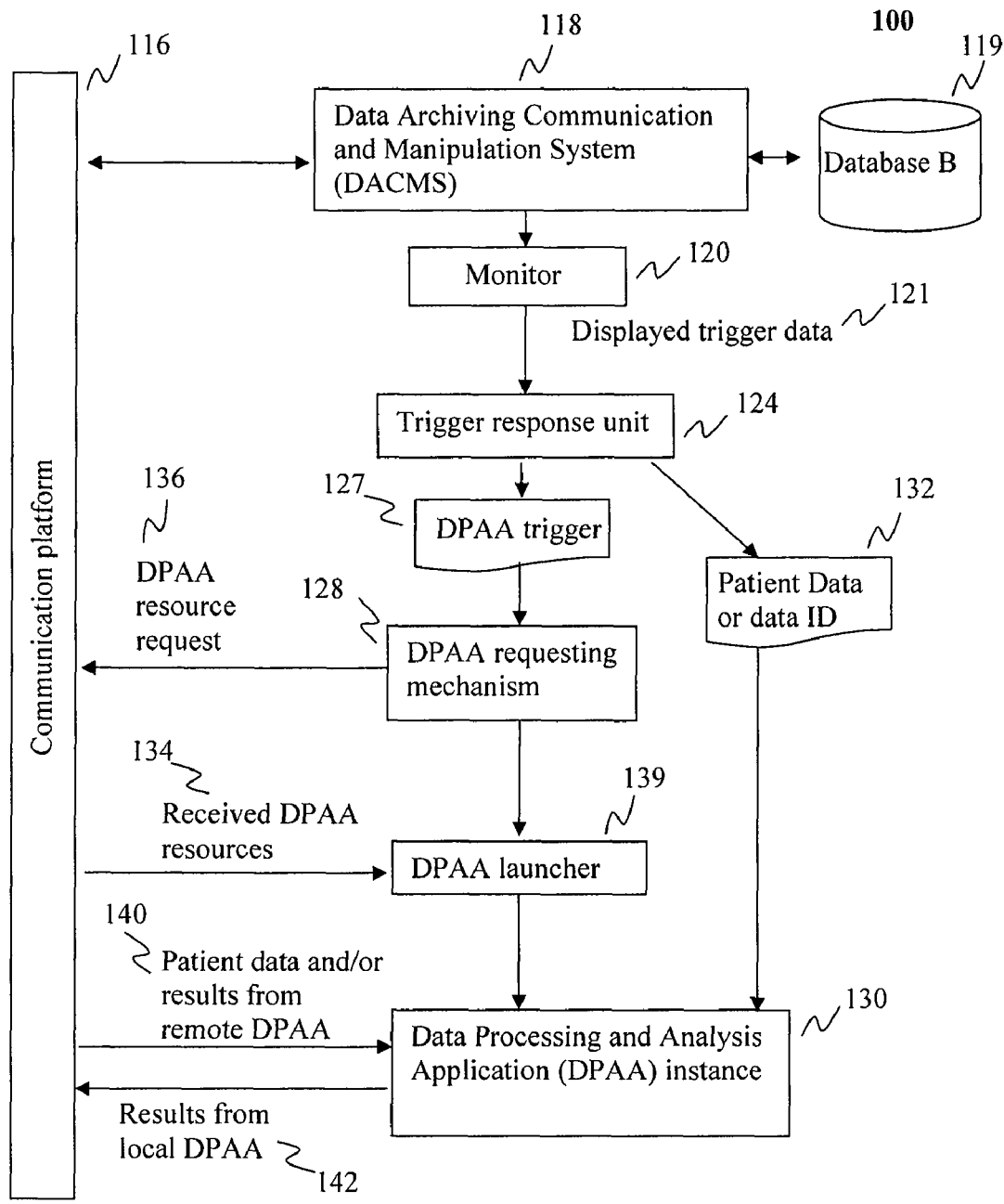

FIG. 1a and FIG. 1b shows an exemplary system diagram 100 facilitating process communication and data/process sharing, according to an embodiment of the current teaching. The system 100 involves two different applications or systems, one is on the left of the communication platform 116 corresponding to the first system and the other is on the right of the communication platform 116 corresponding to the second system. The two applications may or may not reside in separate computing devices. The system 100 comprises components of the first system including a Data Processing and Analysis Application (DPAA) unit 102, a DPAA representation unit 105, a trigger data generation unit 110, a communication unit 114, a communication platform 116, and additionally all the parts residing on the second system, including a Data Archiving Communication and Manipulation System (DACMS) 118, a trigger response unit 124, a DPAA requesting mechanism 128, a DPAA launching unit 139, which creates an instance of DPAA 130. The system 100 further comprises an image acquisition device 101 for acquiring image data of patients.

The DPAA 102 may process patient data 108 from a data storage database A 104. The database A 104 may store both original patient data and processed result data. It may store data of different types, including, but not limited to, patient record, patient report, digital images, such as X-ray, CT, MRI, and results of data processing. The original data may be sent directly from the image acquisition device 101 or retrieved from the DACMS 118. The DPAA may be represented, through the DPAA representation unit 105, as a DPAA trigger 106. The DPAA trigger 106 may be in the form of a symbolic or numeric representation of the DPAA such as an abstraction in the form of an identification number to be used by the first system to identify DPAA or a physical location representing where the DPAA is stored. For example, a symbolic representation of a DPAA trigger may be a character string such as "ABC". When there are multiple application systems to be shared within, e.g., DACMS, an identification number for each of such application systems may be defined to uniquely identify a specific application system.

The trigger data generation unit 110 may generate a trigger data 112 containing the DPAA trigger 106 and a patient data ID (identity) for each patient data 108. The trigger data 112 may be exported via the communication unit 114 to the DACMS unit 118 via a communication platform 116. Standardized protocols such as a DICOM overlay object, a DICOM secondary capture, a DICOM Structured Report (SR), or a DICOM image, may be used to facilitate the transportation.

The DACMS 118 may be any system or application that performs certain functions, including, but not limited to, data storage, data communication, data processing, and data visualization. An example of such a system is a Picture Archiving and Communicating System (PACS). The DACMS 118 may store the trigger data into a data storage Database B, 119. If DPAA 102 and DACMS 118 are located in different computers, the communication platform 116 may be either a local area network (LAN), or a wide area network (WAN) or other types of communication media. If the DPAA 102 and DACMS 118 are both located on the same computer, the communication platform 116 may include, but not limited to, specific hard drive locations or a specific network port number.

The trigger response unit 124 may be designed to correspond to a functional block of the first system such as the illustrated DPAA application system. The trigger response unit 124 is deployed within a foreign environment such as the second application system, e.g., the DACMS system, as shown in FIG. 1b. Once being deployed on the second system, the trigger response unit 124 monitors when a trigger data is displayed on a screen, e.g., monitor 120, in the foreign environment (e.g., DACMS). When the trigger data is displayed, e.g., upon a physicians' selection, on a monitor 120, the trigger response unit 124 detects the presence of a trigger pattern and extracts or decodes both the DPAA trigger 127 and the patient data or data ID 132 from the displayed trigger data 121.

In order to be deployed on the second system, the trigger response unit 124 may be pre-loaded in the second system or the environment, prior to the second application system such as DACMS starts to display the trigger data exported from the first application system such as DPAA. The deployment of the trigger response unit 124 may be through a direct installation, download, or remote deployment from DPAA 102. Based upon the extracted DPAA trigger 127, the DPAA requesting mechanism 128 may send a DPAA resource request 136 to the communication platform 116. The DPAA source request 136 may incorporate the decoded DPAA trigger which, upon being received by the first system, can be used by the first system to instantiate an instance of the DPAA and send DPAA resources 134 to the DPAA launcher 139. Upon receiving the DPAA resources 134, the DPAA launcher 139 may then launch such created instance of DPAA 130 in the DACMS environment.

The DPAA launcher 139 may be an independent program running in the backend in the DACMS environment. When an instance of DPAA 130 is launched, the activated DPAA instance may then be used to manipulate the patient data imported from the first application system or DPAA. If additional analysis results are subsequently generated by the original first DPAA, the launched DPAA in the foreign environment may send a request for the results to be sent to the launched DPAA 130. The communications between the original DPAA and the launched DPAA in the foreign environment may be based on the patient data ID 132.

On the other hand, if some information needed by the launched DPAA is not present in the trigger image, the launched DPAA may request such information from either the original DPAA 102 residing on the first system or from DACMS 118 through some standard interfaces, such as DICOM. In this way, both DACMS and DPAA can operate on the same patient data. The processed results 142 from the launched DPAA on the second system may also be sent to DACMS 118 and remote DPAA 102 via the communication platform 116.

Figure 2A:
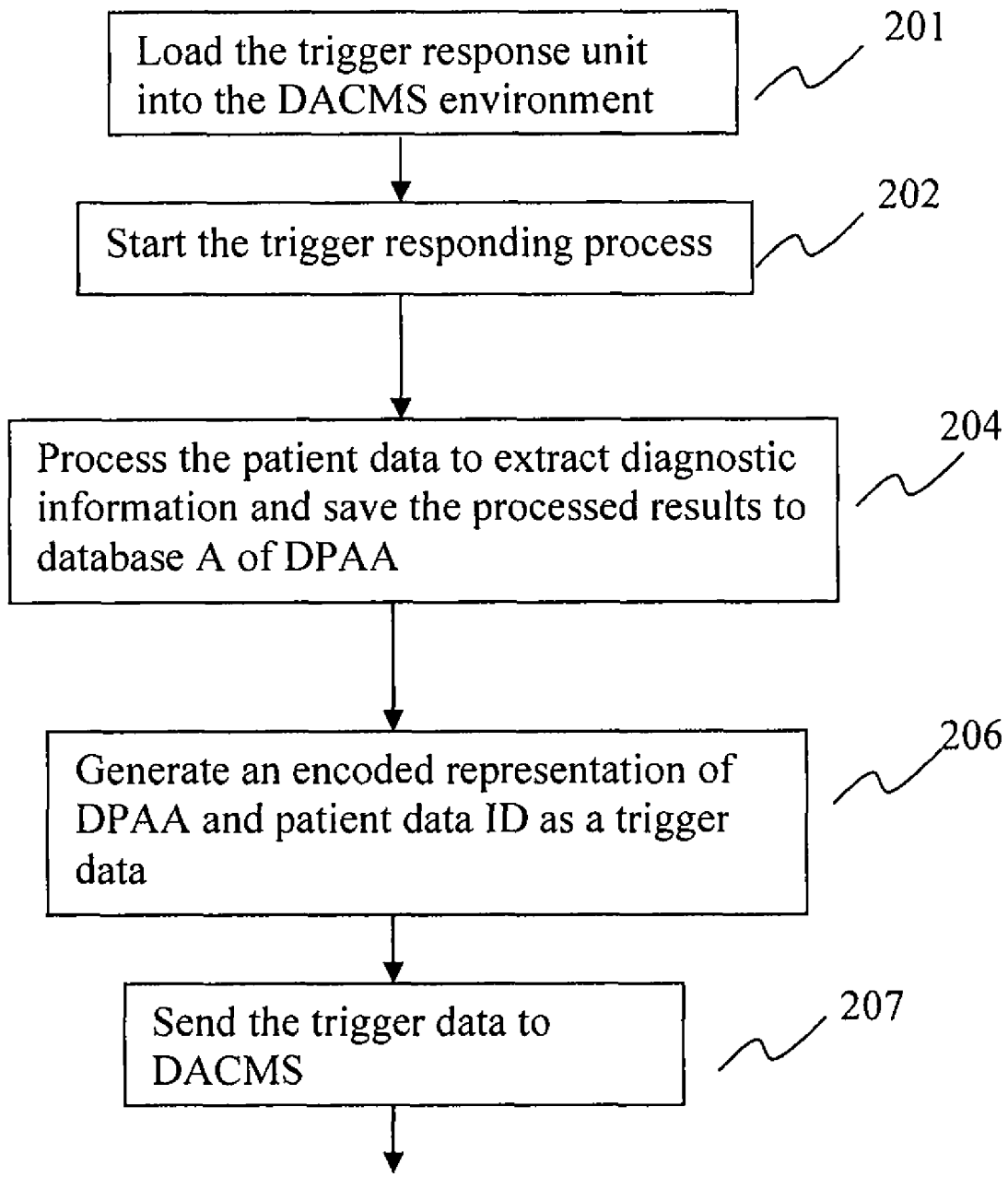
FIGS. 2a and 2b show a flowchart of process communication and process sharing between multiple systems/applications, according to an embodiment of the present teaching.
Figure 2B:
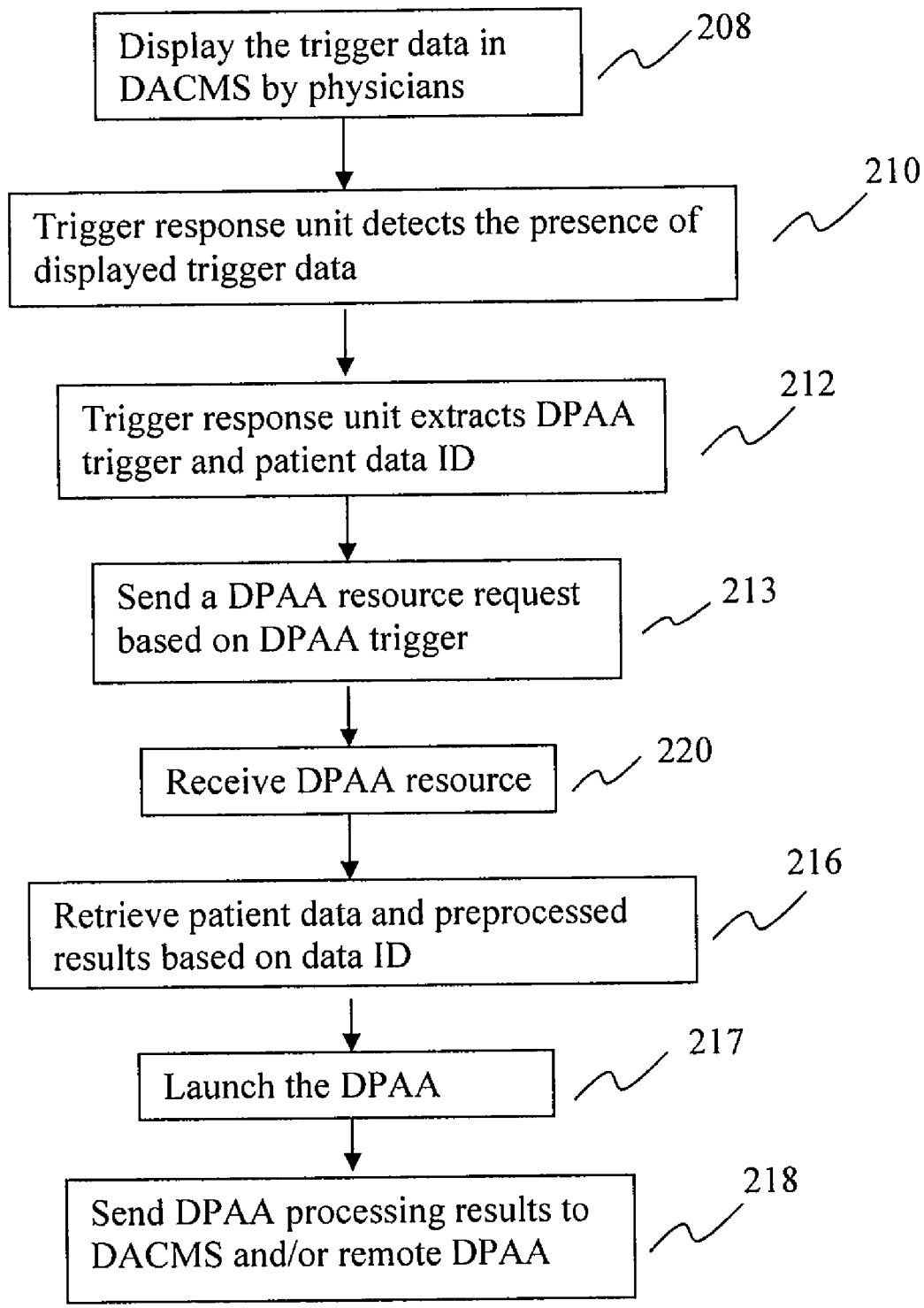

FIGS. 2a and 2b illustrates an exemplary workflow of the system 100, according to one embodiment of the present teaching. At step 201, the trigger response unit 124 may be deployed in the DACMS environment, either remotely from the DPAA environment or through local installation. Upon being deployed in the DACMS environment, the trigger response unit may then, at step 202, start to monitor when a trigger data created by a DPAA system is displayed in the DACMS environment. It may check for the existence of a trigger pattern on a display screen. Such checking may be performed within a memory, in which the DACMS program may reside and operate. The check may also be performed in a buffer that stores data to be displayed. The memory may include video memory.

After the trigger response unit 124 is deployed in a foreign environment, the process/data sharing may be facilitated in the following steps. At step 204, the DPAA system may process each patient data to extract diagnostic information and save the results to the database A 104 of DPAA. At step 206, the trigger generation unit may generate a trigger data containing both DPAA trigger 106 and the patient data ID. At step 207, the trigger data may be sent to the DACMS 118 by the communication unit 114. At step 208, physicians may open the trigger data and displays it on the screen in DACMS. When the trigger data is displayed in the DACMS environment, the trigger response unit 124 detects the presence of a trigger pattern at step 210 and extracts the DPAA trigger and patient data ID at step 212, e.g., by a process running on the backend in DACMS environment. At step 213, a request for DPAA resources is generated based on the extracted DPAA trigger and sent to the original DPAA. Upon receiving the DPAA resource request, the original DPAA 102 responds to the request by sending the requested DPAA resources at step 220.

At step 216, the patient data and the associated preprocessing results may be retrieved from the remote DPAA 102, based on the extracted data ID. When DPAA components and the patient data are available, a DPAA instance may be instantiated and launched at step 217. At step 218, the processed results from the launched DPAA may be sent to DACMS or to the original DPAA.

Figure 3:
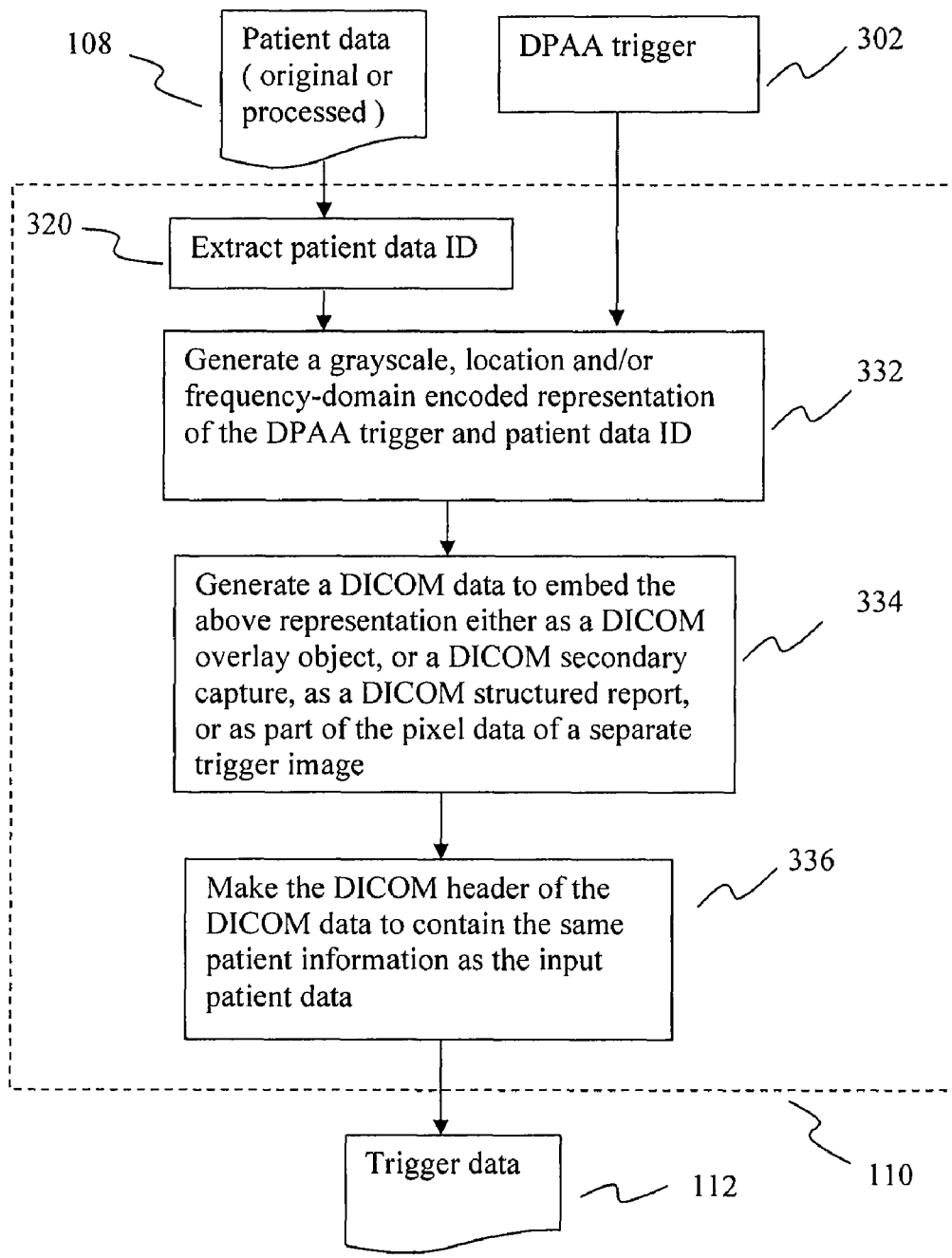
FIG. 3 is an exemplary flow of trigger data generation, according to an embodiment of the present teaching.

FIG. 3 is an exemplary flowchart of trigger data generation unit 110 according to an embodiment of the present teaching. At step 320, the patient data ID may be extracted from the patient data 108. In some embodiments, the SOP (Service Object Pair) instance UID (Unique Identifier) is extracted from the DICOM header of the patient data 108. The SOP instance UID is designed by the DICOM standard to uniquely identify a patient image. At step 332, the DPAA trigger 302 and patient data ID may be encoded into locations, grayscales and frequency domain of a set of encoding objects and/or images. At step 334, the encoded DPAA trigger and patient data ID may be represented either as a standalone DICOM overlay object, or a DICOM secondary capture, a DICOM SR, or a separate DICOM image. At step 336, the DICOM object is made to contain the same patient information as the original data. The output is a trigger data 112 that contains both DPAA trigger and patient data ID.

Figure 4A:
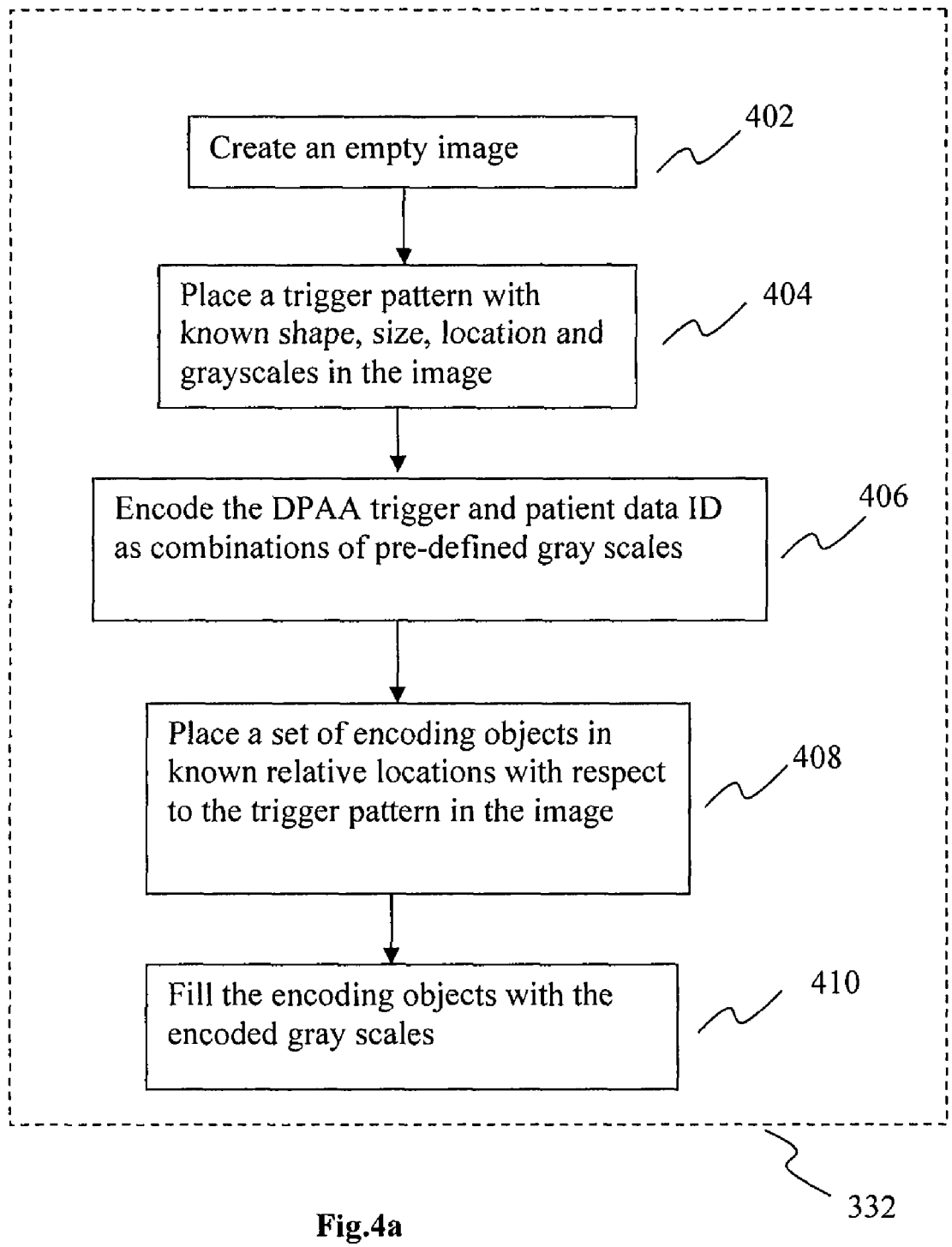
FIG. 4a shows an exemplary embodiment of encoding of DPAA trigger and patient data ID into locations and grayscales of encoding objects, according to an embodiment of the present teaching.
Figure 4B:
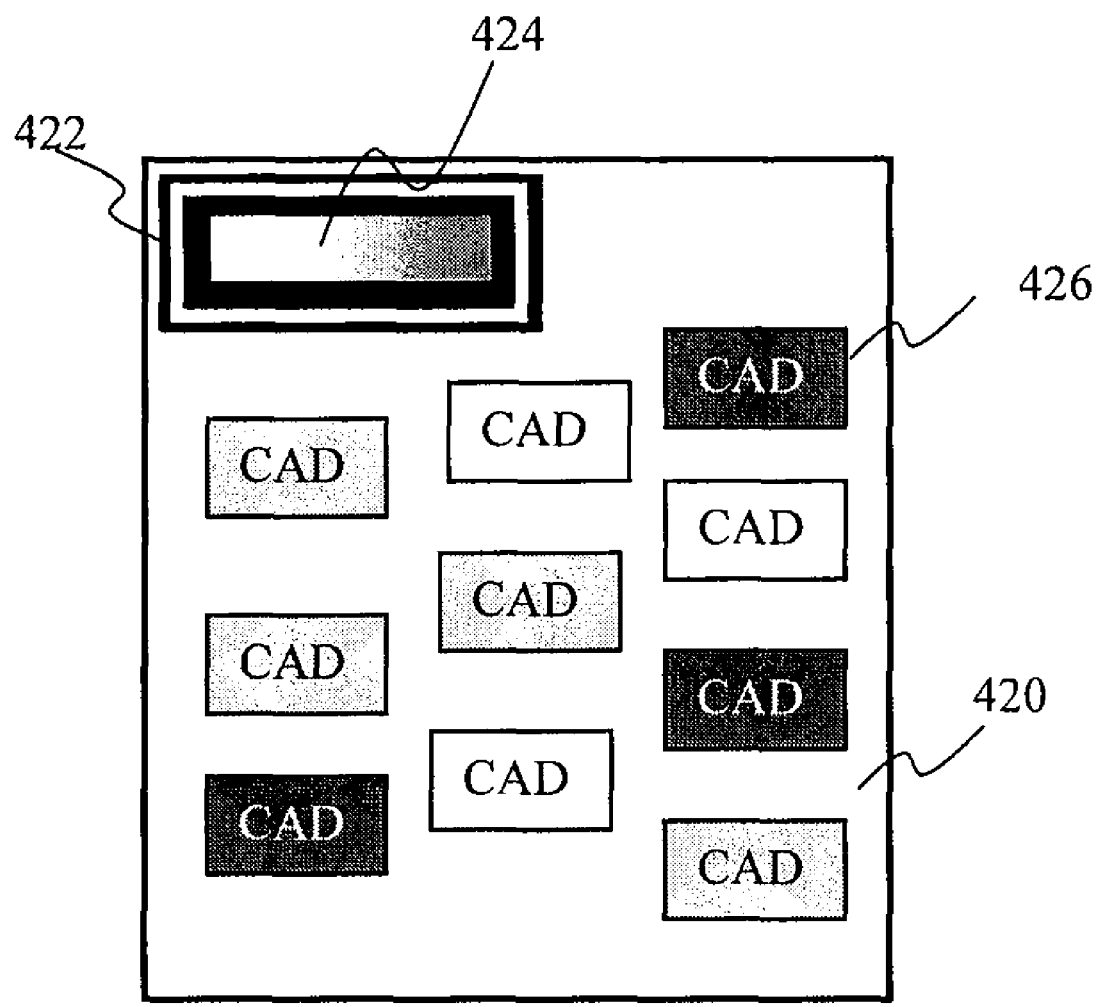
FIG. 4b is an exemplary construct of a trigger pattern and encoding objects, according to an embodiment of the present teaching.

FIG. 4a illustrates an exemplary flowchart of the DPAA trigger and patient data ID representation unit 332, in terms of grayscales and positions of a set of encoding objects. At step 402, an empty image is created. At step 404, a trigger pattern with known shape configuration, size and intensity configuration is generated. The trigger pattern may have a uniquely identifiable shape and grayscale pattern, which may not be commonly seen in medical images. FIG. 4b shows an exemplary trigger pattern 422 with black/white borders, filled with grayscales 424 of known distribution. At step 406, a DPAA trigger and patient data ID may be encoded as combinations of pre-defined grayscales. For example, 4 levels of grayscales within grayscale 100, e.g., 0, 30, 60, 100, may be used to represent the decimal digits 0 to 9, as follows: 0_0 for 0, 0_30 for 1, 0_60 for 2, 0_100 for 3, 30_0 for 4, 30_30 for 5, 30_60 for 6, 30_100 for 7, 60_0 for 8, 60_30 for 9, where the symbol "_" represents 'and'. A set of encoding objects may be placed, at step 408, in known relative positions with respect to the trigger pattern. The encoding objects are then filled with encoded grayscales at step 410. The trigger pattern may also be combined with the encoding objects, e.g., by encompassing the encoding objects with a specific graphic pattern.

FIG. 4b shows an exemplary embodiment of spatial domain encoding in terms of ten encoding objects 426 as illustrated in 420. Each encoding object 426 is represented as a, e.g., a rectangular object at a certain location of the image. The pixels in each rectangular object has uniform intensity values determined based on an intensity encoding scheme described herein. For example, in FIG. 4b, there are 10 rectangular objects 426. There are four levels of intensity values used, 0, 30, 60, and 100, with 0 representing the darkest grayscale. In this particular example, when reading column-wise from left to right, the grayscales are 30, 30, 0, 100, 30, 100, 0, 100, 0, and 60. When the neighboring grayscales are pair-wise combined, the resulting grayscales 30_30, 0_100, 30_100, 0_100, 0_60 may represent the decimal string 53732, where the first digits 5 may be used to represent a DPAA identity, and the rest digits 3732 may represents a patient data ID.

Figure 5:
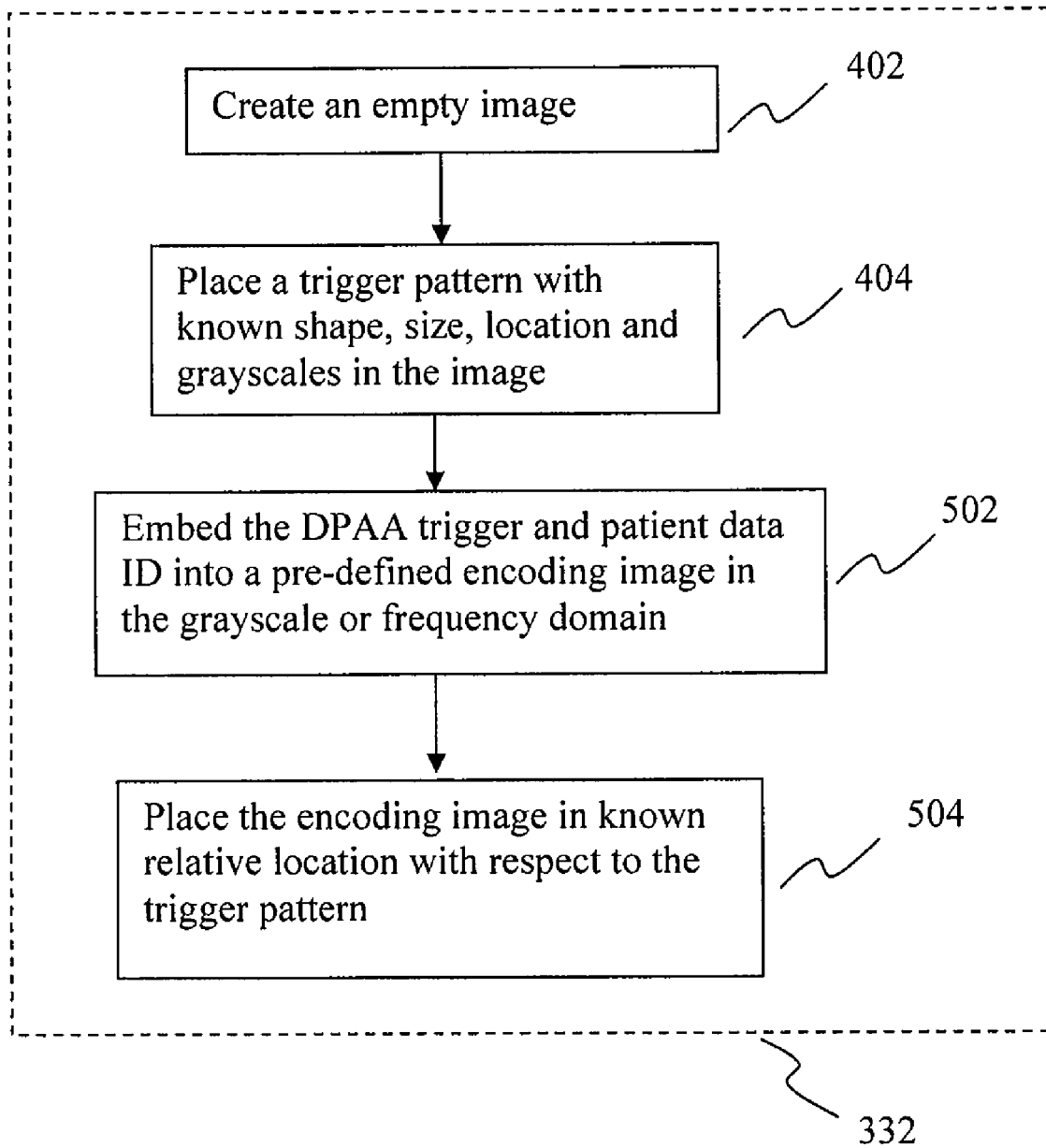
FIG. 5 shows an exemplary embodiment of encoding of DPAA trigger and patient data ID into grayscale and frequency domains of an encoding image, according to an embodiment of the present teaching.

In some embodiments, spatial intensity based encoding can be used. In other embodiments, alternative encoding scheme such as frequency domain coding scheme may also be used. FIG. 5 illustrates another exemplary flowchart of the DPAA trigger and patient data ID representation unit 332, in terms of frequency domain encoding. At steps 402 and 404, an empty image and a trigger pattern may be generated. At step 502, the DPAA trigger and patient data ID may be embedded in the grayscale or frequency domain of an encoding image. An exemplary embodiment of grayscale or frequency domain encoding may be based on watermark techniques, where information may be embedded, either visibly or non-visibly, into an image. A survey of such techniques can be found in F. A. P. Petitcolas, R. J. Anderson, M. G. Kuhn, "Information hiding—A survey", Proceedings of IEEE, 87(7):1062-1078, 1999, At step 504, the encoding image may be placed in known relative position with respect to the trigger pattern. The trigger pattern may also be combined with the encoding image. For example, the encoding image may be circumscribed with a specific graphic pattern to be easily detectable, and the grayscales of part of the encoding image may be taken as the grayscales of the trigger pattern.

Figure 6:
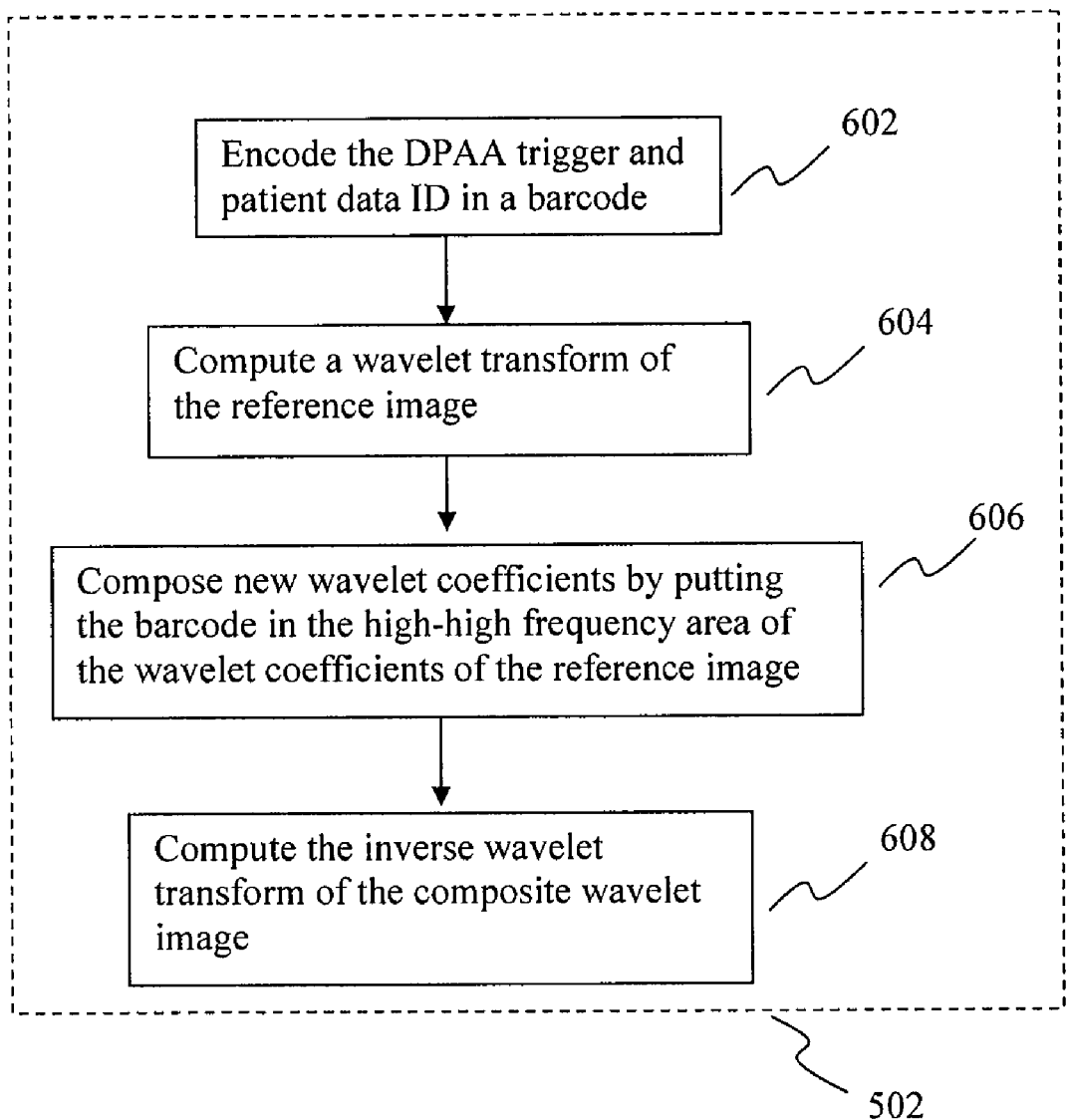
FIG. 6 shows an exemplary flow of embedding of a bar-code-encoded DPAA trigger and patient data ID into the wavelet coefficients of an encoding image, according to an embodiment of the present teaching.

FIG. 6 illustrates an exemplary embodiment of the grayscale and frequency domain encoding unit 502 in terms of wavelet transform. At step 602, a DPAA trigger and a patient data ID may be encoded in barcode, as disclosed in U.S. patent application Ser. No. 11/785,413 on "Methods for enabling an application within another independent system/application in medical imaging" by J. Z. Qian, F. Ma, G. Q. Wei, C. C. Liang, L. Fan, X. Zeng. At step 604, a pre-selected encoding image is transformed by a wavelet transform. The result of the wavelet transform is a set of frequency-domain coefficients arranged in the LL (low-low), LH (low-high), HL (high-low) and HH (high-high) quadtree. Depending on the number of levels of the transform, the LL sub-band coefficients may be recursively decomposed. At step 606, the HH sub-band of wavelet coefficients may be replaced by the barcode image to form a new set of wavelet coefficients. The barcode image may be designed to fit the size of the HH subband. The new wavelet coefficients may then be inversely transformed, at step 608, to the grayscale domain to obtain a new image, which encodes the DPAA trigger and patient data ID. The encoded information may not be visually recognizable though human eyes.

Figure 7A:
FIG. 7a illustrates an exemplary encoding image.
Figure 7B:
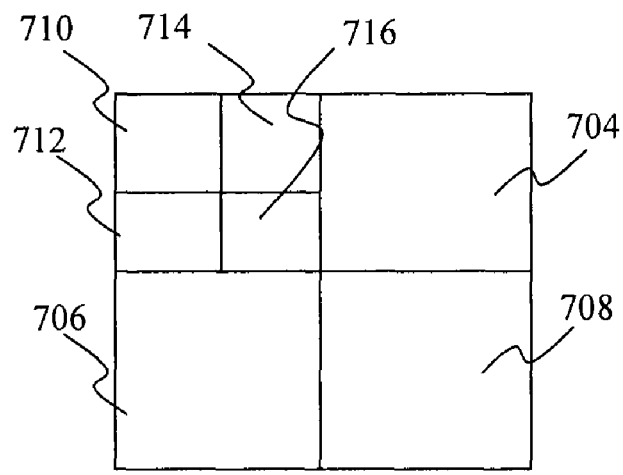
Figure 7C:
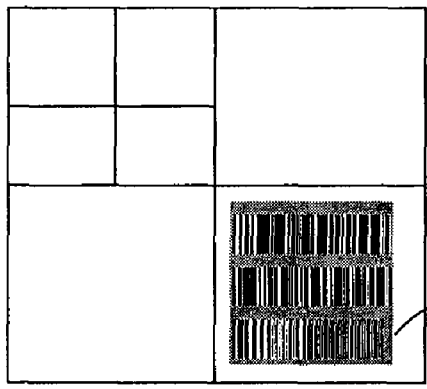
FIG. 7c shows an embodiment of how the wavelet coefficients may be modified by replacing the HH subband of the wavelet transform with a barcode image, according to an embodiment of the present teaching.
Figure 7D:
FIG. 7d shows the inverse transform of the modified wavelet coefficients of FIG. 7c.

FIGS. 7*a*-7*d* illustrate an example of wavelet-based encoding, according to an embodiment of the present teaching. FIG. 7*a* shows s a, exemplary trigger pattern. FIG. 7*b* shows quadtree subbands of a 2-level wavelet transform of FIG. 7*a*, where areas 710, 712, 714, 716 form the LL subband of the 1$^{st}$ level, 704 the LH subband of the 1$^{st}$ level, 706 the HL subband of the 1$^{st}$ level, and 708 the HH subband of the 1$^{st}$ level. Areas 710, 712, 714, and 716 form the LL, LH, HL, and HH subbands of the 2$^{nd}$ level of the transform. FIG. 7*c* shows a set of modified wavelet coefficients subbands, with 1$^{st}$ level HH-subband replaced by a barcode image 718. The barcode image 718 encodes a DPAA trigger and a patient data ID. FIG. 7*d* shows the inverse transformation of the wavelet coefficients of FIG. 7*c*. The barcode image is encoded in the frequency domain, and becomes invisible in the image domain.

Since the trigger data contains the same patient information as the original image, it may be organized under the same patient into the data storage unit 120 by the DACMS 118, according to the DICOM protocol.

Figure 8:
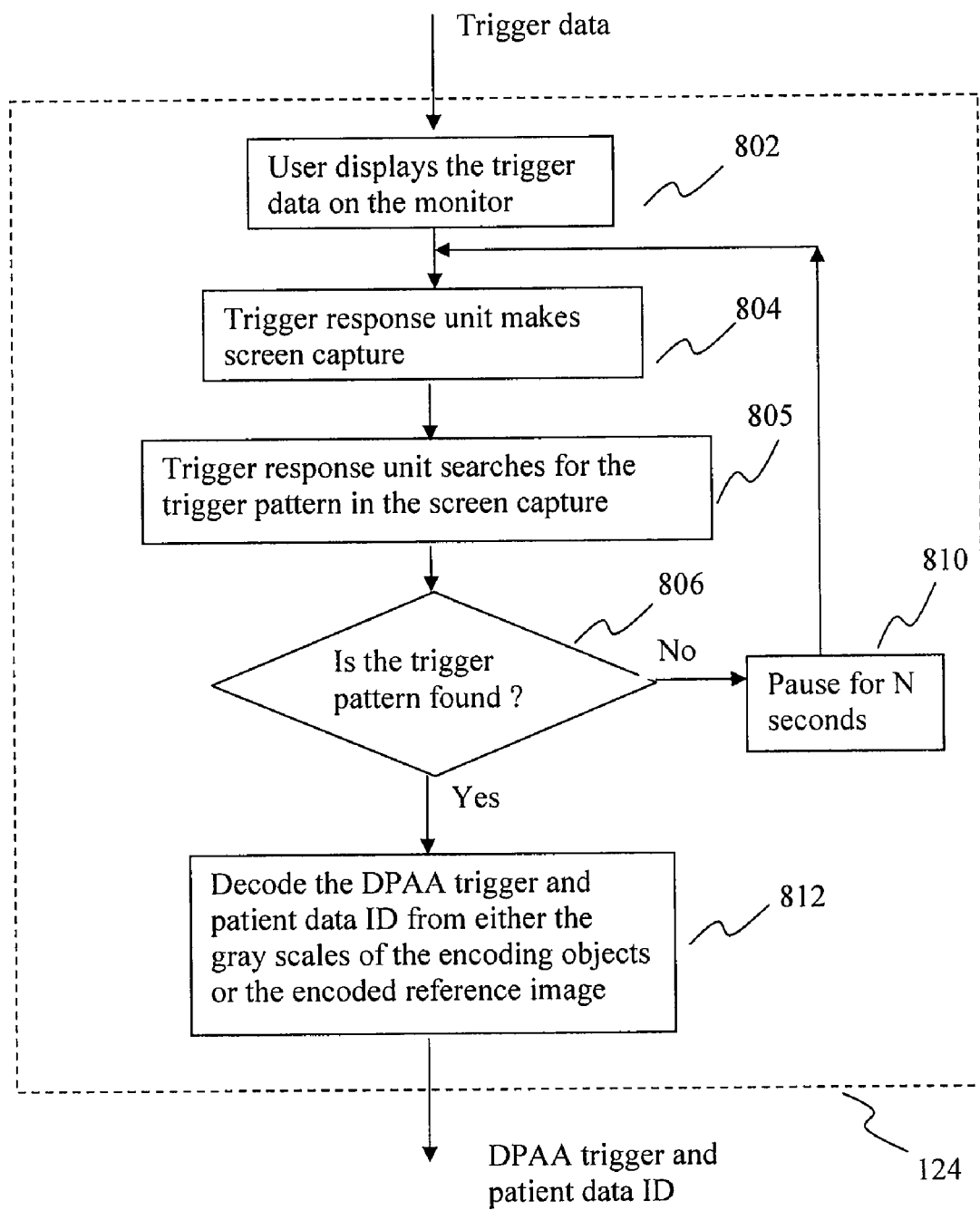
FIG. 8 is an exemplary embodiment of a trigger response unit for extracting a DPAA trigger and associated patient data ID from a trigger data, according to an embodiment of the present teaching.

FIG. 8 shows an exemplary flow of the trigger response unit 124. At step 802, a user selects to display a trigger data in the environment of DACMS 118. Depending on the implementation of DACMS, the selection may be performed either by double-clicking a thumbnail of the trigger data, or by clicking an entry in the image list of the patient data.

The previously deployed trigger response unit, running in the backend of the DACMS environment, may make screen captures of the display monitor, at step 804. The capture may be performed at sampled screen locations, based on known location of the trigger pattern within the trigger data. At step 805, the captured regions may then be analyzed to identify whether the trigger pattern is present on the screen. If it is determined, at step 806, that no trigger pattern is present, the trigger response unit may pause for a certain time interval at step 810 and subsequently capture another screen capture to search for the trigger pattern. If the expected trigger pattern is captured and identified, it may then be analyzed so that the DPAA trigger and patient data ID can be decoded and extracted, at step 812. Depending on how the DPAA trigger and patient data ID are encoded, corresponding decoding techniques may be used for extracting the DPAA trigger and the patient data ID.

Figure 9:
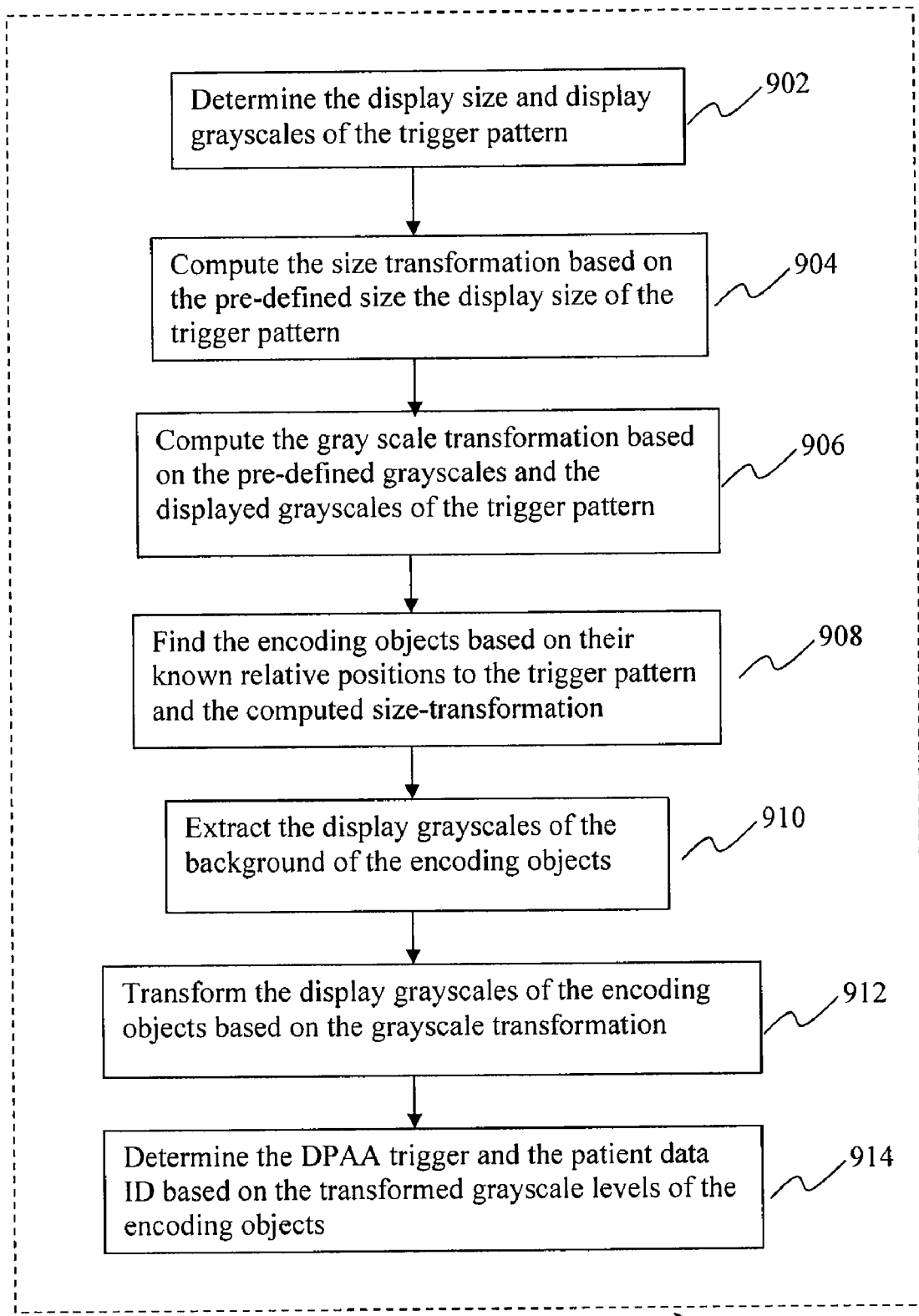
FIG. 9 shows an exemplary flow of a decoding unit for extracting a DPAA trigger and patient data ID, corresponding to an encoding based on grayscales and locations of the encoding objects, according to an embodiment of the present teaching.

FIG. 9 illustrates an exemplary flowchart of the decoding unit 812, corresponding to the encoding method of FIG. 4*a*. At step 902, the displayed size and displayed grayscales of the trigger pattern are determined. Depending on the monitor resolution and the monitor color setting, the displayed size and grayscales of the trigger pattern may be different from ones at design time. From the displayed size and the designed size of the trigger pattern, the transformation between the display size and design size may be found. This transformation is usually a scaling transformation. At step 906, based on the correspondences of displayed grayscales and designed grayscales of the trigger pattern, the grayscale transformation between the displayed grayscale and designed grayscale of the trigger pattern may be computed. The transformation is usually a shift plus a scaling. At step 908, the encoding objects may be localized based on their relative positions to the trigger pattern and the computed size transformation. The grayscales of the encoding objects may then be extracted at step 910. Based on the grayscale transformation, the displayed grayscales of the encoding objects may be transformed to the grayscales at design time, at step 912. Based on the grayscale encoding rules, the DPAA trigger and patient data ID may be found at step 914.

Figure 10:
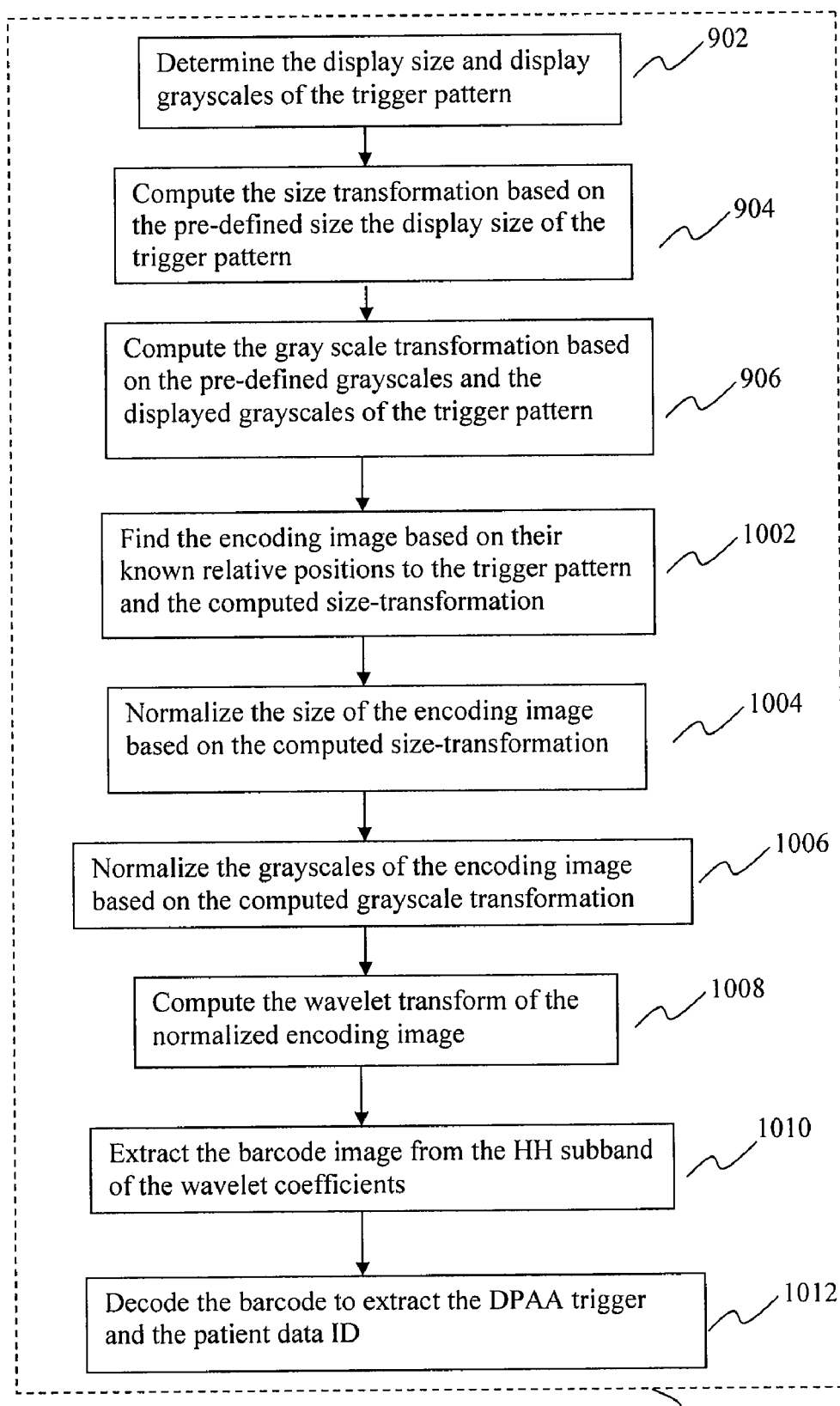
FIG. 10 shows an exemplary flow of a decoding unit for extracting a DPAA trigger and patient data ID, corresponding to an encoding based on wavelet coefficients of an encoding image, according to an embodiment of the present teaching.

FIG. 10 illustrates an exemplary flowchart of the decoding unit 812, corresponding to the wavelet-based encoding method in FIG. 6. Steps 902 to 906 are the same as those described in FIG. 9. At step 1002, the encoding image is localized based on its relative position to the trigger pattern and the size transformation computed at step 904. At step 1004, the displayed image size of the encoding image is normalized to the designed size based on the computed size transformation. At step 1006, the displayed grayscales of the encoding image are transformed to the grayscales at design time, based on the computed grayscale transformation at step 906. At step 1008, the wavelet transformation of the normalized encoding image is performed. From the subband of the wavelet coefficients, the barcode image may then be extracted at step 1010. From the extracted barcode image, standard barcode decoding techniques may be applied to decode the DPAA trigger and patient data ID at step 1012.

While the inventions have been described with reference to the certain illustrated embodiments, the words that have been used herein are words of description, rather than words of limitation. Changes may be made, within the purview of the appended claims, without departing from the scope and spirit of the invention in its aspects. Although the inventions have been described herein with reference to particular structures, acts, and materials, the invention is not to be limited to the particulars disclosed, but rather can be embodied in a wide variety of forms, some of which may be quite different from those of the disclosed embodiments, and extends to all equivalent structures, acts, and, materials, such as are within the scope of the appended claims.

We claim:

1. A method implemented on at least one machine each of which has at least one processor, storage, and communication platform for data/process sharing, comprising:
    deploying a trigger response unit on a first system where a first application resides;
    detecting, by the trigger response unit, the presence of a representation of trigger data in the first application, wherein the trigger data is from a second application residing on a second system;
    decoding the detected representation of the trigger data to obtain a trigger, wherein the representation encodes the trigger corresponding to the second application and associated information; and
    launching the second application within the first application on the first system based on the trigger when the trigger data has been graphically rendered as a trigger pattern by the first application on the first system, wherein the trigger data include the trigger pattern spatially configured in a trigger image and encoded based on intensity levels.

2. The method according to claim 1, wherein the trigger data is generated on the second system by:
   obtaining an encoded representation of the trigger and the associated information to be encoded; and
   generating a data format that embeds the encoded representation.

3. The method according to claim 2, wherein the step of obtaining the encoded representation comprises:
   generating an image;
   generating the trigger pattern;
   inserting the generated trigger pattern at a pre-defined coordinate in the image; and
   embedding the trigger and the associated information into a plurality of encoding objects, each of which has a pre-determined shape and size and the number of encoding object is determined based on the trigger and the associated information, wherein
   the encoding objects form a spatial configuration in which the encoding objects have a pre-determined geographical relationship with each other, and
   the encoding objects code the trigger and the associated information based on intensity values determined based on the trigger and the associated information.

4. The method according to claim 3, wherein the trigger pattern has a pre-determined size and shape.

5. The method according to claim 1, wherein the step of decoding comprises:
   determining a display size and intensity levels of the trigger pattern;
   deriving a size transformation based on a pre-defined size and the display size of the trigger pattern;
   deriving an intensity transformation based on pre-defined intensity levels and the display intensity levels of the trigger pattern;
   identifying encoding objects based on their positions relative to the trigger pattern and the size transformation;
   extracting the display intensity levels from the encoding objects; transforming the display intensity levels extracted from the encoding objects based on the intensity transformation to obtain transformed intensity levels; and
   determining the trigger and the associated information based on the transformed intensity levels.

6. A method implemented on at least one machine each of which has at least one processor, storage, and communication platform for data/process sharing, comprising:
   deploying a trigger response unit on a first system where a first application resides;
   detecting, by the trigger response unit, the presence of a representation of trigger data in the first application, wherein the trigger data is from a second application residing on a second system;
   decoding the detected representation of the trigger data to obtain a trigger, wherein the representation encodes the trigger corresponding to the second application and information associated with data; and
   launching the second application within the first application on the first system based on the trigger when the trigger data has been graphically rendered as a trigger pattern by the first application on the first system, wherein
   the trigger data include the trigger pattern embedded in a trigger image based on frequency domain transformation.

7. The method according to claim 6, further comprising:
   sending a resource request by the first system to the second system for at least a portion of the second application in accordance with the trigger; and
   receiving the at least a portion of the second application from the second system.

8. The method according to claim 7, wherein the associated information includes the patient data and an identification of the patient data.

9. The method according to claim 6, wherein trigger data is generated on the second system by:
   obtaining an encoded representation of the trigger and the associated information to be encoded; and
   generating a data format that embeds the encoded representation.

10. The method according to claim 9, wherein
    the data format is Digital Imaging and Communication in Medicine (DICOM); and
    when DICOM is embedded with the encoded representation, it includes the associated information in a header.

11. The method according to claim 10, wherein when the encoded representation is embedded in DICOM, it is embedded as one of a DICOM overlay object, a DICOM secondary capture, and a DICOM structured report.

12. The method according to claim 9, wherein the encoded representation is embedded as a part of pixel data of the trigger image.

13. The method according to claim 9, wherein the trigger data is generated by performing the steps of:
    generating an image;
    generating the trigger pattern in the image;
    embedding the trigger and the associated information in a pre-defined encoding image; and
    inserting the encoding image at a pre-determined location with respect to the trigger pattern in the image.

14. The method according to claim 13, wherein the pre-defined encoding image is a barcode.

15. The method according to claim 13, wherein the trigger pattern has a pre-determined size and shape.

16. The method according to claim 13, wherein the step of embedding comprises:
    encoding the trigger and the associated information in the pre-defined encoding image;
    performing a transformation of the trigger pattern from spatial domain to frequency domain to produce a frequency domain representation of the trigger pattern;
    replacing a pre-determined portion of the frequency domain representation of the trigger pattern using the encoding image to produce a composite representation; and
    computing an inverse transformation of the composite representation to derive the trigger data.

17. The method according to claim 16, wherein the transformation is a wavelet transformation and the frequency domain representation is a wavelet coefficient image.

18. The method according to claim 16, wherein the pre-determined portion of the frequency domain representation corresponds to a range of frequencies.

19. The method according to claim 18, wherein the range corresponds to a quadtree of the frequency domain representation.

20. The method according to claim 6, wherein the step of decoding comprises:
    determining a display size and intensity levels of the trigger pattern;
    deriving a size transformation based on a pre-defined size and the display size of the trigger pattern;

deriving an intensity transformation based on pre-defined intensity levels and the display intensity levels of the trigger pattern;

identifying an encoding image based on a position relative to the trigger pattern and the size transformation; performing a normalization on the size of the encoding image based on the size transformation;

performing a normalization of the intensity levels of the encoding image based on the intensity transformation to produce a normalized encoding image;

computing a frequency domain transformation image of the normalized encoding image with transformation coefficients;

extracting a sub-image from a pre-determined region of the frequency domain transformation image; and decoding the sub-image to extract the trigger and the associated information.

21. The method according to claim 20, wherein the sub-image is a barcode.

22. The method according to claim 20, wherein the pre-determined region corresponds to a range of frequencies represented in a quadtree of the frequency domain transformation image.

23. The method according to claim 22, wherein the quadtree in the frequency domain transformation image corresponds to a high-high frequency range.

24. A method implemented on at least one machine each of which has at least one processor, storage, and communication platform for data/process sharing, comprising:

generating a representation corresponding to trigger data from a second application residing on a second system, wherein the trigger data is to be used to trigger the second application in a first application residing on a first system;

receiving, by a second system, a resource request sent by the first application from the first system for at least a portion of the second application;

sending, by the second system, the portion of the second application in accordance with the resource request, wherein the resource request is sent after the presence of the representation for the trigger data is detected by a trigger response unit deployed on the first system, the second application is launched in the first application on the first system when the trigger data has been graphically rendered as a trigger pattern by the first application on the first system, and the trigger data include the trigger pattern spatially configured in an image and encoded based on intensity values.

25. The method according to claim 24, wherein the step of generating comprises:

obtaining the representation of the trigger data including a trigger and information of data to be encoded; and generating a data format that embeds the representation.

26. The method according to claim 25, wherein the data format is Digital Imaging and Communication in Medicine (DICOM); and when DICOM is embedded with the representation, it includes the associated information in a header.

27. A method implemented at least one machine each of which has at least one processor, storage, and communication platform for data/process sharing, comprising:

generating a representation corresponding to trigger data from a second application residing on a second system, wherein the trigger data is to be used to trigger the second application in a first application residing on a first system;

receiving, by a second system, a resource request sent by the first application from the first system for at least a portion of the second application;

sending, by the second system, the portion of the second application in accordance with the resource request, wherein the resource request is sent after the presence of the representation for the trigger data is detected by a trigger response unit deployed on the first system, the second application is launched in the first application on the first system when the trigger data has been graphically rendered as a trigger pattern by the first application on the first system, and the trigger data include the trigger pattern spatially configured in an image and encoded based on frequency domain transformation.

28. The method according to claim 27, wherein the step of generating comprises:

obtaining the representation of the trigger data including a trigger and information of data to be encoded; and generating a data format that embeds the representation.

29. The method according to claim 28, wherein the data format is Digital Imaging and Communication in Medicine (DICOM); and when DICOM is embedded with the representation, it includes the associated information in a header.

* * * * *